(12) United States Patent
Bullis et al.

(10) Patent No.: US 12,367,580 B2
(45) Date of Patent: *Jul. 22, 2025

(54) METHOD OF DESIGNING AND FABRICATING PATIENT-SPECIFIC RESTORATIONS FROM INTRA-ORAL SCANNING OF A DIGITAL IMPRESSION COPING

(71) Applicant: James R. Glidewell Dental Ceramics, Inc., Newport Beach, CA (US)

(72) Inventors: Grant Bullis, Newport Beach, CA (US); Tao Nguyen, Anaheim, CA (US); Greg Minzenmayer, Foothill Ranch, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/506,715

(22) Filed: Nov. 10, 2023

(65) Prior Publication Data
US 2024/0078674 A1 Mar. 7, 2024

Related U.S. Application Data

(63) Continuation of application No. 17/353,105, filed on Jun. 21, 2021, now Pat. No. 11,816,835, which is a
(Continued)

(51) Int. Cl.
*G06K 9/00* (2022.01)
*A61B 5/055* (2006.01)
(Continued)

(52) U.S. Cl.
CPC ............ *G06T 7/0012* (2013.01); *A61B 5/055* (2013.01); *A61B 6/51* (2024.01); *A61C 8/0001* (2013.01);
(Continued)

(58) Field of Classification Search
CPC ..... G06T 7/0012; A61B 5/055; A61C 8/0001; A61C 9/004; G06V 2201/031
See application file for complete search history.

(56) References Cited

U.S. PATENT DOCUMENTS

| 4,769,349 A | 9/1988 | Hillig et al. |
| 4,772,436 A | 9/1988 | Tyszblat |

(Continued)

FOREIGN PATENT DOCUMENTS

| CA | 2762187 | 12/2010 |
| DE | 1471423 B | 12/1969 |

(Continued)

OTHER PUBLICATIONS

International Search Report for PCT/US2010/001532 dated Oct. 25, 2010.
(Continued)

*Primary Examiner* — Jayesh A Patel
(74) *Attorney, Agent, or Firm* — Klarquist Sparkman, LLP

(57) ABSTRACT

Taking a digital implant or abutment level digital impression by means of intra-oral, computed tomography or other imaging method provides the restorative doctor and laboratory accurate and effective data for determining the implant position, angulation and locking feature orientation without a physical impression. Such data is correlated with a digital library to produce an output which enables design and fabrication of an accurate restorative device such as a prosthetic tooth or crown. In this way the time-consuming, costly and error prone mechanical replication of the relevant dental anatomy is obviated.

3 Claims, 3 Drawing Sheets

Related U.S. Application Data continuation of application No. 16/740,769, filed on Jan. 13, 2020, now Pat. No. 11,042,979, which is a continuation of application No. 14/516,981, filed on Oct. 17, 2014, now Pat. No. 10,561,478, which is a continuation of application No. 12/800,784, filed on May 21, 2010, now Pat. No. 8,867,800.

(60) Provisional application No. 61/217,186, filed on May 27, 2009.

(51) Int. Cl.
    *A61B 6/51*     (2024.01)
    *A61C 8/00*     (2006.01)
    *A61C 9/00*     (2006.01)
    *A61C 13/00*     (2006.01)
    *G06T 7/00*     (2017.01)
    *G16H 20/40*     (2018.01)

(52) U.S. Cl.
    CPC .......... *A61C 9/004* (2013.01); *A61C 13/0004* (2013.01); *G06T 2207/30004* (2013.01); *G06V 2201/031* (2022.01); *G16H 20/40* (2018.01)

(56) References Cited

U.S. PATENT DOCUMENTS

| | | | |
|---|---|---|---|
| 4,992,297 A | 2/1991 | Van Der Zel | |
| 5,052,929 A | 10/1991 | Seal | |
| 5,213,502 A * | 5/1993 | Daftary | A61C 8/00 433/172 |
| 5,296,175 A | 3/1994 | Iwasaki et al. | |
| 5,395,437 A | 3/1995 | Chiou | |
| 5,401,170 A | 3/1995 | Nonomura | |
| 5,441,408 A | 8/1995 | Moschik | |
| 5,443,770 A | 8/1995 | Krstic et al. | |
| 5,662,476 A | 9/1997 | Ingber et al. | |
| 5,672,055 A | 9/1997 | Koutavas | |
| 5,674,073 A | 10/1997 | Ingber et al. | |
| 5,698,019 A | 12/1997 | Frank et al. | |
| 5,785,911 A | 7/1998 | Willkens et al. | |
| 5,904,483 A | 5/1999 | Wade | |
| 5,944,526 A | 8/1999 | Liu | |
| 5,968,856 A | 10/1999 | Schweiger et al. | |
| 5,975,905 A | 11/1999 | Kim et al. | |
| 5,989,029 A | 11/1999 | Osorio et al. | |
| 6,007,926 A | 12/1999 | Provenzano et al. | |
| 6,135,773 A | 10/2000 | Lazzara | |
| 6,305,939 B1 | 10/2001 | Dawood | |
| 6,342,458 B1 | 1/2002 | Schweiger et al. | |
| 6,364,660 B1 | 4/2002 | Durbin et al. | |
| 6,386,867 B1 | 5/2002 | Durbin et al. | |
| 6,386,876 B1 | 5/2002 | Lee | |
| 6,420,288 B2 | 7/2002 | Schweiger et al. | |
| 6,431,800 B1 | 8/2002 | Suzuki | |
| 6,455,451 B1 | 9/2002 | Brodkin et al. | |
| 6,514,893 B1 | 2/2003 | Schweiger et al. | |
| 6,517,623 B1 | 2/2003 | Brodkin et al. | |
| 6,565,357 B1 | 5/2003 | Lazzara et al. | |
| 6,592,371 B2 | 7/2003 | Durbin et al. | |
| 6,788,986 B1 * | 9/2004 | Traber | A61C 8/0048 700/98 |
| 6,802,894 B2 | 10/2004 | Brodkin et al. | |
| 6,824,386 B2 * | 11/2004 | Halldin | A61C 8/0001 433/173 |
| 6,878,456 B2 | 4/2005 | Castro et al. | |
| 6,882,894 B2 | 4/2005 | Durbin et al. | |
| 7,118,375 B2 | 10/2006 | Durbin et al. | |
| 7,271,100 B2 | 9/2007 | Lee et al. | |
| 7,312,924 B2 | 12/2007 | Trissel | |
| 7,322,824 B2 | 1/2008 | Schmitt | |
| 7,328,077 B2 | 2/2008 | Durbin et al. | |
| 7,351,060 B2 | 4/2008 | Chih-Chung | |
| 7,381,258 B2 | 6/2008 | Krumbholz | |
| 7,494,338 B2 | 2/2009 | Durbin et al. | |
| 7,654,823 B2 | 2/2010 | Dadi | |
| 7,655,586 B1 | 2/2010 | Brodkin et al. | |
| 7,661,956 B2 * | 2/2010 | Powell | A61C 13/0004 433/172 |
| 7,672,504 B2 | 3/2010 | Childers | |
| 7,892,995 B2 | 2/2011 | Castillo | |
| 8,077,942 B2 | 12/2011 | Yau et al. | |
| 8,682,043 B2 | 3/2014 | Cahill et al. | |
| 8,867,800 B2 * | 10/2014 | Bullis | G06T 7/0012 382/128 |
| 8,932,058 B2 | 1/2015 | Fisker et al. | |
| 9,364,299 B2 | 6/2016 | Marlin | |
| 10,561,478 B2 | 2/2020 | Bullis et al. | |
| 11,042,979 B2 | 6/2021 | Bullis et al. | |
| 2001/0048969 A1 | 12/2001 | Castantino et al. | |
| 2001/0053512 A1 | 12/2001 | Nichinonni | |
| 2002/0028425 A1 | 3/2002 | Hurson | |
| 2002/0039717 A1 | 4/2002 | Amber et al. | |
| 2002/0055082 A1 | 5/2002 | Durbin et al. | |
| 2003/0082499 A1 | 5/2003 | Halldin et al. | |
| 2003/0096214 A1 | 5/2003 | Luthardt et al. | |
| 2004/0119180 A1 | 6/2004 | Frank et al. | |
| 2004/0133293 A1 | 7/2004 | Durbin et al. | |
| 2004/0197738 A1 | 10/2004 | Ban et al. | |
| 2005/0153257 A1 | 7/2005 | Durbin et al. | |
| 2005/0155518 A1 | 7/2005 | Krumbholz | |
| 2005/0177261 A1 | 8/2005 | Durbin et al. | |
| 2005/0203231 A1 | 9/2005 | Halpert et al. | |
| 2005/0261795 A1 | 11/2005 | Ghosh et al. | |
| 2005/0288165 A1 | 12/2005 | Krumbholz | |
| 2006/0014390 A1 | 1/2006 | Lee et al. | |
| 2006/0019219 A1 | 1/2006 | Saliger et al. | |
| 2006/0115793 A1 | 6/2006 | Kopelman et al. | |
| 2006/0115795 A1 | 6/2006 | Marshal et al. | |
| 2006/0154198 A1 | 7/2006 | Durbin et al. | |
| 2006/0183082 A1 | 8/2006 | Quadling et al. | |
| 2006/0188844 A1 | 8/2006 | Dadi | |
| 2007/0047079 A1 | 3/2007 | Trissel | |
| 2007/0056467 A1 | 3/2007 | Panzera | |
| 2007/0059661 A1 | 3/2007 | Dadi | |
| 2007/0064242 A1 | 3/2007 | Childers | |
| 2007/0092854 A1 | 4/2007 | Powell et al. | |
| 2007/0134496 A1 | 6/2007 | Katagiri et al. | |
| 2007/0160953 A1 * | 7/2007 | Tardieu | A61C 8/0001 433/173 |
| 2007/0218426 A1 | 9/2007 | Quadling et al. | |
| 2008/0010085 A1 | 1/2008 | Hahn | |
| 2008/0050700 A1 * | 2/2008 | Weber | A61C 5/77 433/223 |
| 2008/0085489 A1 | 4/2008 | Schmitt | |
| 2008/0176188 A1 | 7/2008 | Holzner et al. | |
| 2008/0261176 A1 | 10/2008 | Hurson | |
| 2009/0087817 A1 * | 4/2009 | Jansen | A61C 9/0053 433/223 |
| 2009/0104583 A1 | 4/2009 | Yau et al. | |
| 2009/0115084 A1 | 5/2009 | Moon | |
| 2009/0220916 A1 | 9/2009 | Fisker et al. | |
| 2009/0256274 A1 | 10/2009 | Castillo | |
| 2009/0258778 A1 | 10/2009 | Castillo | |
| 2009/0274999 A1 | 11/2009 | Coopersmith | |
| 2010/0083706 A1 | 4/2010 | Castillo | |
| 2010/0112520 A1 | 5/2010 | Worthington | |
| 2010/0112521 A1 | 5/2010 | Chapel | |
| 2010/0112527 A1 | 5/2010 | Chapel | |
| 2010/0255445 A1 | 10/2010 | Gantes | |
| 2011/0081627 A1 | 4/2011 | Sun et al. | |
| 2011/0123954 A1 | 5/2011 | Yau et al. | |
| 2011/0262884 A1 | 10/2011 | Zena et al. | |
| 2012/0270179 A1 | 10/2012 | Holmstrom et al. | |
| 2014/0162214 A1 | 6/2014 | Jansen et al. | |

FOREIGN PATENT DOCUMENTS

| | | |
|---|---|---|
| EP | 1618854 A1 | 1/2006 |
| JP | 06007377 A | 1/1994 |
| JP | H0780004 A * | 3/1995 |
| JP | 11019910 A | 1/1999 |

(56) References Cited

FOREIGN PATENT DOCUMENTS

| | | | | | |
|---|---|---|---|---|---|
| JP | 2009101124 | A | | 5/2009 | |
| KR | 20090028372 | A | | 3/2009 | |
| WO | WO-9714372 | A1 | * | 4/1997 | ............. A61C 8/005 |
| WO | 0134057 | A1 | | 5/2001 | |
| WO | 2006024098 | A1 | | 3/2006 | |
| WO | WO-2007048257 | A1 | * | 5/2007 | ........... A61C 8/0001 |
| WO | 2008138644 | A1 | | 11/2008 | |
| WO | 2009042888 | A2 | | 4/2009 | |
| WO | 2009060415 | A2 | | 5/2009 | |
| WO | 2010138175 | A1 | | 12/2010 | |

OTHER PUBLICATIONS

Final Rejection for U.S. Appl. No. 12/800,784 dated Mar. 22, 2013.
Non-Final Rejection for U.S. Appl. No. 12/800,784 dated Sep. 17, 2012.
Non-Final Rejection for U.S. Appl. No. 12/800,784 dated Dec. 13, 2012.
Notice of Allowability for U.S. Appl. No. 12/800,784 dated Jun. 20, 2014.
International Preliminary Report on Patentability for PCT No. PCT/US2010/001532 dated Nov. 29, 2011, in 5 pages.
Michael Block et al., Single tooth immediate provisional restoration—Results, Dental Implants, 0278-2391, 2004, pp. 1131-1138.
Extended European Search Report for PCT/US2010001532 dated Sep. 26, 2017, in 11 pages.
Perng-Ru Liu, DMD, MS, A Panorama of Dental CAD/CAM Restorative Systems, CE3, Compendium /Jul. 2005, vol. 26, No. 7., pp. 507-513.
E. Dianne Rekow et al., CAD/CAM for Dental Restorations—Some of the Curious Challenges, IEEE Transactions on BioMedical Engineering, vol. 38., No. 4, Apr. 1991, pp. 314-318.
G. Uzun, An Overview of Dental CAD/CAM Systems, Biotechnology & Biotechnological Equipment, 22:1, 530-535, DOI: 10.1080/13102818.2008.10817506, Hacettepe University, School of Dental Technology, Sihhiye, Ankara, Turkey, ISSN:1310-2818 (Print) 1314-3530 (Online) Journal homepage: https:/www.tandfonline.com/loi/tbeq20, pp. 530-535.
Docket Entries for Opposition to EP243498, in 393 pages.

* cited by examiner

METHOD OF DESIGNING AND FABRICATING PATIENT-SPECIFIC RESTORATIONS FROM INTRA-ORAL SCANNING OF A DIGITAL IMPRESSION COPING

CROSS-REFERENCE TO RELATED APPLICATIONS

This application is a continuation of U.S. patent application Ser. No. 17/353,105, filed on Jun. 21, 2021, which is a continuation of U.S. patent application Ser. No. 16/740,769, filed on Jan. 13, 2020, now U.S. Pat. No. 11,042,979, which is a continuation of U.S. patent application Ser. No. 14/516,981, filed on Oct. 17, 2014, now U.S. Pat. No. 10,561,478, which is a continuation of U.S. patent application Ser. No. 12/800,784, filed on May 21, 2010, now U.S. Pat. No. 8,867,800, which claims priority to and the benefit of U.S. Provisional Application No. 61/217,186, filed on May 27, 2009, the entireties of these applications are incorporated herein by reference.

FIELD OF THE INVENTION

The present invention relates to the design and manufacture of patient-specific dental restorations. More specifically, the invention herein relates to restorations such as implant abutments, screw-retained crowns, implant and abutment over-denture and temporary prostheses at the implant and abutment level.

BACKGROUND DISCUSSION

Dental implants have become the preferred modern alternative for replacing missing natural teeth. Typically, an implant abutment is secured into the underlying bone tissue terminating within the surrounding gum tissue. Eventually, a dental restoration is secured to the implant. The restoration must be designed to match the surrounding teeth in color, size, shape and orientation so that it looks and functions much as the predecessor natural tooth it replaces. However, because of potential variability in the precise position (angulation and vertical position) and locking orientation of the implant, the design of the restoration is also subject to substantial variability.

Conventionally, the restoration is designed by a laboratory using a physical replication of the dental anatomy. This physical replication is obtained by affixing an impression coping, locked to the underlying implant or abutment and extending above the gum line among the surrounding dental structure. Then the area is replicated using dental laboratory techniques and a model is produced. The laboratory then uses this model to design and fabricate the prosthetic restoration. Unfortunately, these various steps are time consuming, costly and potentially error prone.

SUMMARY OF THE INVENTION

The present invention overcomes the noted deficiencies and disadvantages of the prior art laboratory process. The invention herein entirely obviates the need for a physical replication to be sent to a laboratory to provide information for the design and fabrication of an implant restoration. The invention comprises the following steps:

1. A digital impression coping is affixed to the implant or abutment (for an abutment level digital impression) by means of a screw or it is friction retained. Digital impression copings for computed tomography and related imaging methods are made from radiopaque materials.

2. The digital impression coping(s) and surrounding dental anatomy are then imaged via intra-oral, computed tomography or other imaging technology including magnetic resonance imaging (MRI).

3. The scan of the digital impression coping(s) is correlated with reference impression digital impression coping(s) to determine the implant(s) position, angulation and locking feature orientation.

4. A laboratory then utilizes a CAD program that uses the implant(s) or abutment(s) spatial relation to the patient's oral anatomy to design patient-specific prosthetic restoration(s) and create the output file(s) required for its manufacture.

Taking a digital implant or abutment level digital impression by means of intra-oral, computed tomography or other imaging method provides the restorative doctor and laboratory an accurate and effective means of determining the implant position, angulation and locking feature orientation without a physical impression. This digital impression has applications including, but not limited to:

1. Designing and fabricating patient-specific restorations such as implant abutments, screw-retained crowns, implant and abutment level over-denture restorations and temporary prostheses at the implant and abutment level.

2. As a record of a patient's implant and anatomical spatial data on a specific date.

BRIEF DESCRIPTION OF THE DRAWINGS

The aforementioned objects and advantages of the present invention, as well as additional objects and advantages thereof, will be more fully understood hereinafter as a result of a detailed description of a preferred embodiment when taken in conjunction with the following drawings in which.

DETAILED DESCRIPTION OF A PREFERRED EMBODIMENT

This method of digital implant and abutment level impression taking is similar to conventional methods, but the implant position, angulation and locking feature orientation are captured via intra-oral, computed tomography or other imaging methods instead of with physical impression media. The basic components required to capture an implant or abutment level digital impression and design a restoration from the digital impression are:

1. A digital impression coping of known dimension, for implant or abutment level, with a flat, radius, slot or other geometrically distinct feature, or features, for determining the implant position, angulation and locking feature orientation.

2. An intra-oral, computed tomography or other imaging method that can record the digital impression coping(s) and oral anatomy with sufficient accuracy.

3. A means of correlating the scan of the digital impression coping with a reference digital impression coping thereby deriving the implant(s) position, angulation and locking feature orientation.

4. CAD software to design the implant or abutment level restorations and create an output file(s) for additive or subtractive manufacture of the implant or abutment level prosthetic restoration.

Figure 1:
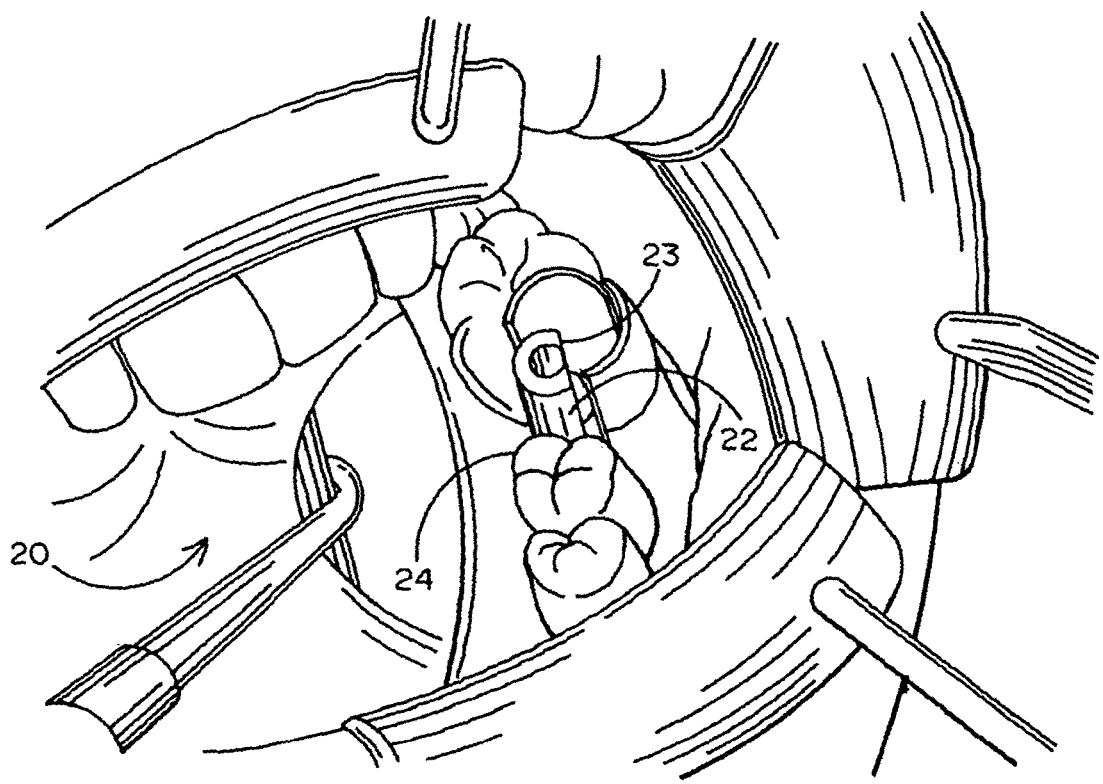
FIG. 1 is a photograph of a patient's oral anatomy adjacent an implant to which a digital impression coping has been affixed and locked into engagement.
Figure 2:
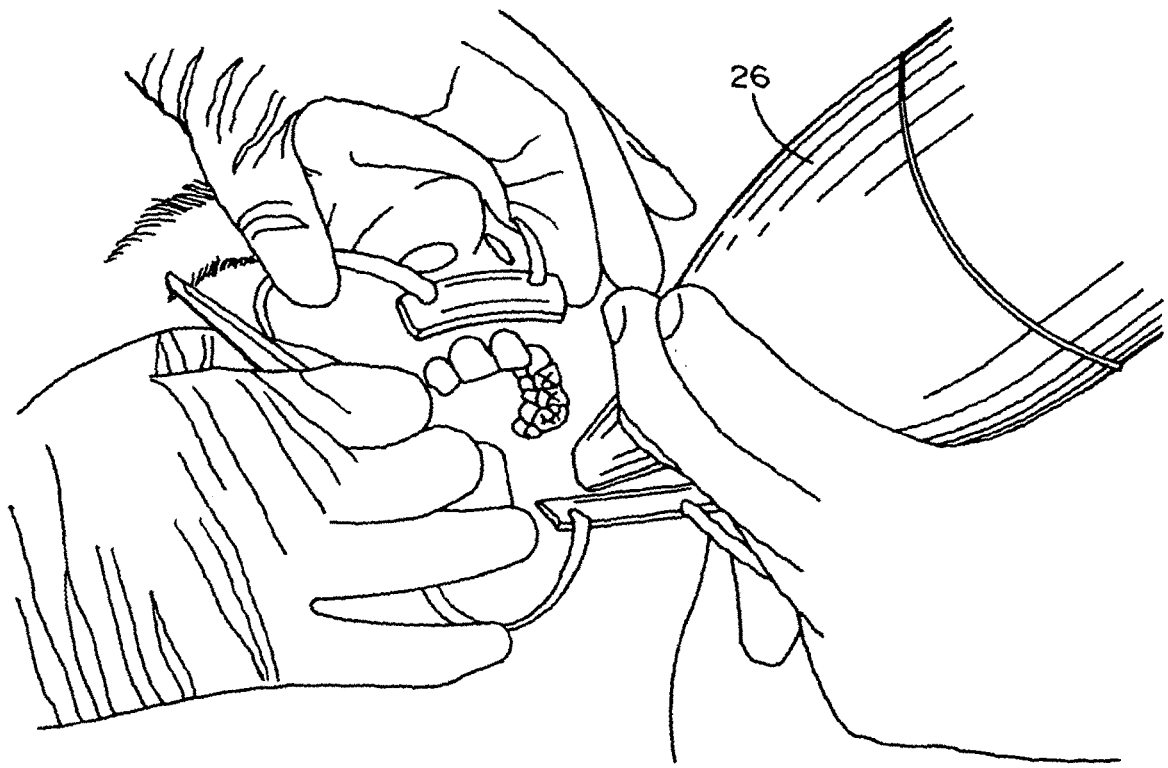
FIG. 2 is a photograph of an intra-oral scanning process of the patient's implant area of FIG. 1.
Figure 3A:
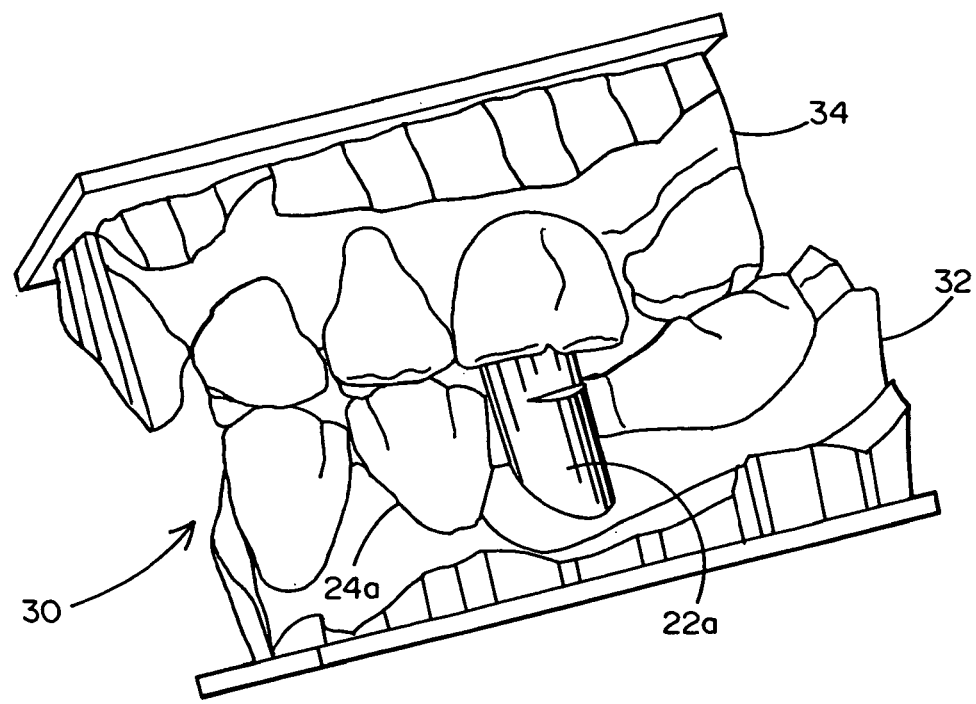
FIGS. 3A and 3B are images obtained by the scanning process of FIG. 2 showing the precise vertical position, angular orientation and locking engagement of the digital impression coping and adjacent dental anatomy.
Figure 3B:
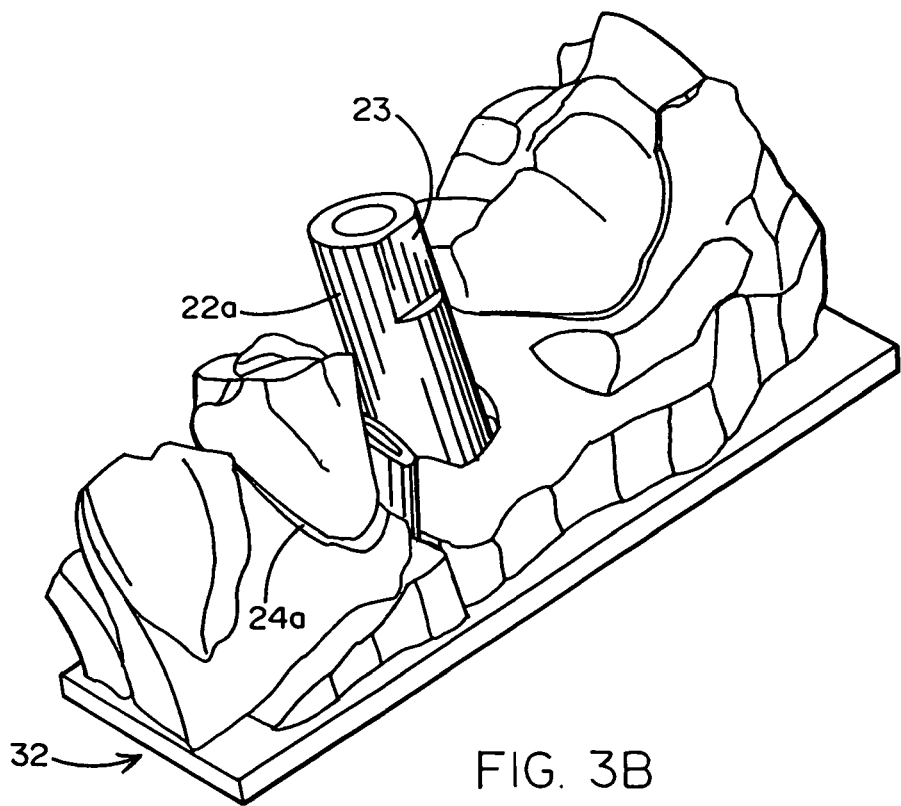

The paragraph 1 component is shown in FIG. 1. As seen therein, a digital impression coping 22 has been affixed to the underlying implant in the oral cavity 20 in an area 24. The abutment is in locking engagement with the implant so that its position and orientation (note the flat area 23 at the upper end of the abutment) will provide precise data in regard to the underlying implant. This data becomes evident in a scan of the area being taken as shown in FIG. 2. A number of available intra-oral scanners 26 are available for performing this step. One such scanner, for example, is an IOS FastScan™ Digital Impression System shown in FIG. 2. The resultant images 30, 32 and 34 are shown in FIGS. 3A and 3B. These images represent the type of data that can be electronically transmitted to a laboratory for the area 24a.

Laboratory personnel maintain a digital library of impression copings that can be correlated to the scan data of the digital impression coping in the patient's mouth. Based upon the digital impression coping length and the location of the "orientating feature" on the upper end of the digital impression coping, three additional types of information can be obtained, namely:

1. The angulation as determined by the angle of the digital impression coping 22a;
2. The position of the implant restorative connection (i.e., its position with respect to the implant-level, or the abutment level and other important fixed points such as adjacent and opposing contacts); and
3. The locking feature orientation (i.e., where the orientating feature on the digital impression coping matches with a corresponding feature 23 on the implant connection).

Figure 4:
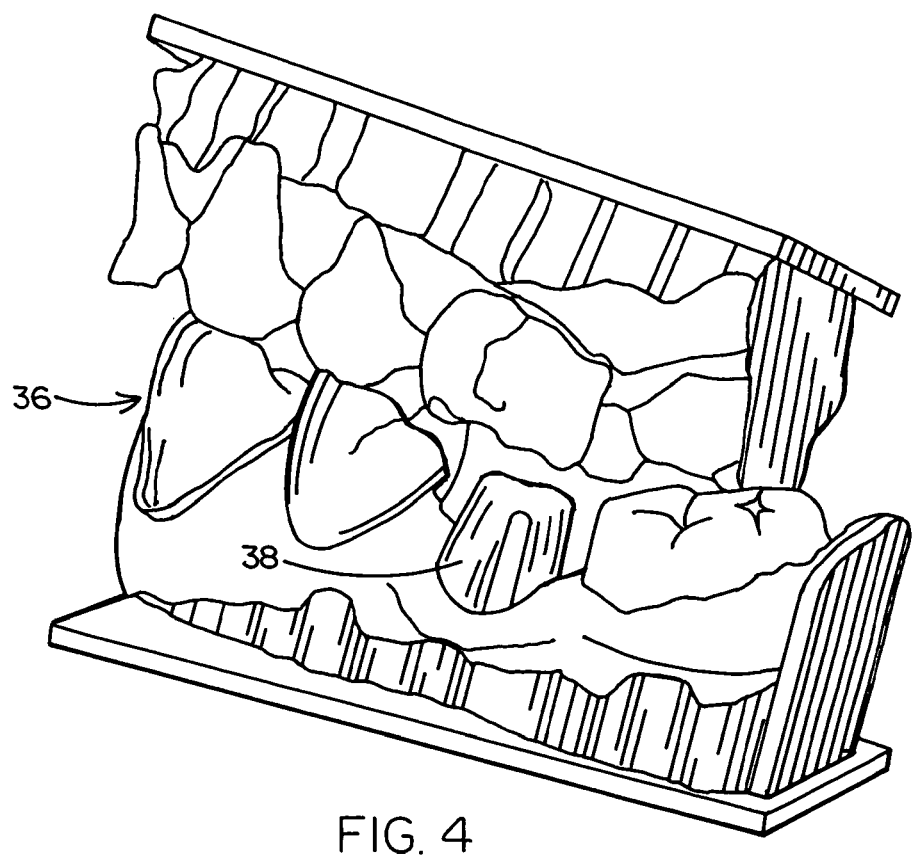
FIG. 4 is an image similar to that of FIGS. 3A and 3B, but showing the oral anatomy with a restoration in place of the digital impression coping and positioned in engagement with the underlying implant ready to receive a prosthetic tooth or crown based upon data derived from the originally scanned image.
Figure 5:
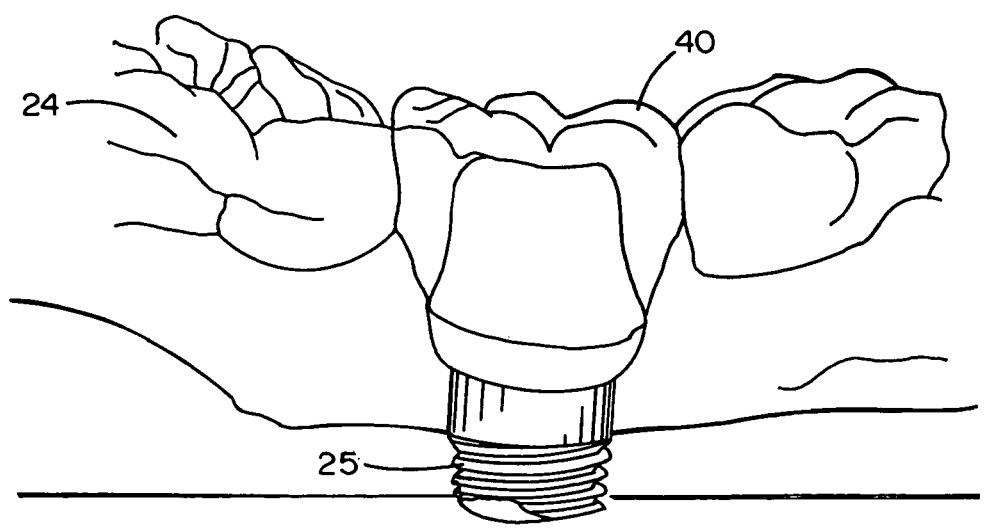
FIG. 5 is an image of the relevant anatomy showing placement of a prosthetic implant abutment, designed and fabricated by employing the present invention.

The laboratory personnel can then employ these data, derived both from the image and from their library, to utilize CAD software to create an output file 36 (see FIG. 4) of the prosthetic restoration 38 from which the physical restoration 40 is then fabricated and sent to the dentist or implant surgeon who mates it with the implant 25 (see FIG. 5).

Having thus disclosed a preferred embodiment of the invention, it will now be apparent that variation from the described example, is contemplated. By way of example, the image may be derived in ways not specifically described herein and the digital impression coping may be configured with various alternative characteristics which alter the data from that specifically disclosed herein. Accordingly, the scope of the invention herein is not necessarily limited to the specific embodiment depicted, but only by the appended claims and their legal equivalents.

The invention claimed is:

1. A method for providing a properly configured dental prosthetic restoration for mating with an implant abutment without requiring a physical impression of a patient's oral cavity, the method comprising the steps of:
   a) mating a digital impression coping with said abutment;
   b) generating a digital image of said coping and adjacent dental anatomy;
   c) creating a library of data representative of a plurality of digital impression copings corresponding to implant abutments of a plurality of different manufacturers; and
   d) using said digital image to configure a restoration to mate with said abutment, including the step of correlating said image to said library for a specific digital impression coping to derive angular and vertical position data and locking orientation.

2. The method recited in claim 1 wherein generating a digital image of said coping and adjacent dental anatomy comprises the step of producing an oral cavity image which includes at least adjacent and opposing teeth of said patient in relation to said implant.

3. The method recited in claim 1 wherein the digital impression coping includes at least one flat, radius, slot, or other geometrically distinct feature for determining the position and angulation of the abutment.

* * * * *